(12) United States Patent  
Piha et al.

(10) Patent No.: US 11,724,116 B2  
(45) Date of Patent: Aug. 15, 2023

(54) WEARABLE CARDIOVERTER DEFIBRILLATOR LATCHING CONNECTOR

(71) Applicant: West Affum Holdings Corp., Grand Cayman (KY)

(72) Inventors: Daniel R. Piha, Bellevue, WA (US); Robert R. Buchanan, Redmond, WA (US); Dallas E. Meeker, Bothell, WA (US); Douglas K. Medema, Everett, WA (US); Quan H. Nguyen, Renton, WA (US)

(73) Assignee: WEST AFFUM HOLDINGS DAC, Dublin (IE)

( * ) Notice: Subject to any disclaimer, the term of this patent is extended or adjusted under 35 U.S.C. 154(b) by 259 days.

(21) Appl. No.: 16/994,525

(22) Filed: Aug. 14, 2020

(65) Prior Publication Data

US 2020/0406044 A1 Dec. 31, 2020

Related U.S. Application Data

(63) Continuation-in-part of application No. 16/277,838, filed on Feb. 15, 2019, now abandoned.  
(Continued)

(51) Int. Cl.  
*A61N 1/37* (2006.01)  
*A61N 1/39* (2006.01)  
(Continued)

(52) U.S. Cl.  
CPC ......... *A61N 1/3904* (2017.08); *A61N 1/3603* (2017.08); *A61N 1/3752* (2013.01);  
(Continued)

(58) Field of Classification Search  
CPC .. A61N 1/3904; A61N 1/3603; A61N 1/3752; A61N 1/3758; A61N 1/3937;  
(Continued)

(56) References Cited

U.S. PATENT DOCUMENTS 3,724,355 A 4/1973 Unger  
4,583,524 A 4/1986 Hutchins  
(Continued)

FOREIGN PATENT DOCUMENTS

EP 3380189 B1 10/2018  
WO 1998039061 A2 9/1998  
WO 2012064604 A1 5/2012

OTHER PUBLICATIONS

Klein, H. U., Goldenberg I., & Moss, A. J., Risk Stratification for Implantable Cardioverter Defibrillator Therapy: The Role of the Wearable Cardioverter-Defibrillator, Clinical update, European Heart Journal, May 31, 2013, pp. 1-14, doi:10.1093/eurheartj/eht167, European Society of Cardiology.  
(Continued)

*Primary Examiner* — Amanda K Hulbert  
*Assistant Examiner* — Natasha Patel  
(74) *Attorney, Agent, or Firm* — Columbia IP Law

(57) ABSTRACT

A wearable cardioverter defibrillator ("WCD") latching connector system includes a receptacle positioned within a WCD monitor, and a connector configured to removably engage the receptacle.

20 Claims, 19 Drawing Sheets

Related U.S. Application Data

(60) Provisional application No. 62/630,995, filed on Feb. 15, 2018.

(51) Int. Cl.
*A61N 1/375* (2006.01)
*A61N 1/36* (2006.01)

(52) U.S. Cl.
CPC ......... *A61N 1/3758* (2013.01); *A61N 1/3937* (2013.01); *A61N 1/3993* (2013.01)

(58) Field of Classification Search
CPC .... A61N 1/3993; A61N 1/046; A61N 1/0472; A61N 1/3968
USPC .......................................................... 607/5
See application file for complete search history.

(56) References Cited

U.S. PATENT DOCUMENTS

| | | | |
|---|---|---|---|
| 4,619,265 A | 10/1986 | Morgan et al. | |
| 4,928,690 A | 5/1990 | Heilman et al. | |
| 4,955,381 A | 9/1990 | Way et al. | |
| 5,078,134 A | 1/1992 | Heilman et al. | |
| 5,228,449 A | 7/1993 | Christ et al. | |
| 5,348,008 A | 9/1994 | Bomn et al. | |
| 5,353,793 A | 10/1994 | Bomn | |
| RE34,800 E | 11/1994 | Hutchins | |
| 5,394,892 A | 3/1995 | Kenny | |
| 5,405,362 A | 4/1995 | Kramer et al. | |
| 5,474,574 A | 12/1995 | Payne et al. | |
| 5,618,208 A * | 4/1997 | Crouse | H01R 13/6593 439/607.17 |
| 5,662,690 A | 9/1997 | Cole et al. | |
| 5,782,878 A | 7/1998 | Morgan et al. | |
| 5,792,204 A | 8/1998 | Snell | |
| 5,902,249 A | 5/1999 | Lyster | |
| 5,913,685 A | 6/1999 | Hutchins | |
| 5,944,669 A | 8/1999 | Kaib | |
| 6,047,203 A | 4/2000 | Sackner et al. | |
| 6,065,154 A | 5/2000 | Hulings et al. | |
| 6,108,197 A | 8/2000 | Janik | |
| 6,148,233 A * | 11/2000 | Owen | A61N 1/0476 607/5 |
| 6,201,992 B1 | 3/2001 | Freeman | |
| 6,263,238 B1 | 7/2001 | Brewer et al. | |
| 6,287,328 B1 | 9/2001 | Snyder et al. | |
| 6,304,780 B1 | 10/2001 | Owen et al. | |
| 6,319,011 B1 | 11/2001 | Motti et al. | |
| 6,334,070 B1 | 12/2001 | Nova et al. | |
| 6,356,785 B1 | 3/2002 | Snyder | |
| 6,427,083 B1 | 7/2002 | Owen et al. | |
| 6,437,083 B1 | 7/2002 | Owen et al. | |
| 6,529,875 B1 | 3/2003 | Nakajima | |
| 6,546,285 B1 | 4/2003 | Owen et al. | |
| 6,671,545 B2 | 12/2003 | Fincke | |
| 6,681,003 B2 | 1/2004 | Linder et al. | |
| 6,762,917 B1 | 7/2004 | Verbiest et al. | |
| 7,065,401 B2 | 6/2006 | Worden | |
| 7,559,902 B2 | 7/2009 | Ting et al. | |
| 7,865,238 B2 | 1/2011 | Brink | |
| 7,870,761 B2 | 1/2011 | Valentine et al. | |
| 7,974,689 B2 | 7/2011 | Volpe et al. | |
| 8,135,462 B2 | 3/2012 | Owen et al. | |
| 8,140,154 B2 | 3/2012 | Donnelly et al. | |
| 8,369,944 B2 | 2/2013 | Macho et al. | |
| 8,548,557 B2 | 10/2013 | Garstka et al. | |
| 8,615,295 B2 | 12/2013 | Savage et al. | |
| 8,644,925 B2 | 2/2014 | Volpe et al. | |
| 8,676,313 B2 | 3/2014 | Volpe et al. | |
| 8,897,860 B2 | 11/2014 | Volpe et al. | |
| 8,904,214 B2 | 12/2014 | Volpe et al. | |
| 8,965,500 B2 | 2/2015 | Macho et al. | |
| 9,008,801 B2 | 4/2015 | Kaib et al. | |
| 9,089,685 B2 | 7/2015 | Sullivan et al. | |
| 9,131,901 B2 | 9/2015 | Volpe et al. | |
| 9,132,267 B2 | 9/2015 | Kaib | |
| 9,408,548 B2 | 8/2016 | Volpe et al. | |
| 9,454,219 B2 | 9/2016 | Volpe et al. | |
| 9,592,403 B2 | 3/2017 | Sullivan | |
| 9,878,171 B2 | 1/2018 | Kaib | |
| 2003/0158593 A1 | 8/2003 | Heilman et al. | |
| 2005/0107833 A1 | 5/2005 | Freeman et al. | |
| 2005/0107834 A1 | 5/2005 | Freeman et al. | |
| 2006/0173499 A1 | 8/2006 | Hampton et al. | |
| 2008/0033495 A1 | 2/2008 | Kumar | |
| 2008/0312709 A1 | 12/2008 | Volpe et al. | |
| 2009/0005827 A1 | 1/2009 | Weintraub et al. | |
| 2009/0187229 A1* | 7/2009 | Lavie | A61N 1/3754 607/36 |
| 2010/0007413 A1 | 1/2010 | Herleikson | |
| 2010/0298899 A1 | 11/2010 | Donnelly et al. | |
| 2011/0022105 A9 | 1/2011 | Owen et al. | |
| 2011/0288604 A1 | 11/2011 | Kaib et al. | |
| 2011/0288605 A1 | 11/2011 | Kaib et al. | |
| 2012/0112903 A1 | 5/2012 | Kaib et al. | |
| 2012/0144551 A1 | 6/2012 | Guldalian | |
| 2012/0150008 A1 | 6/2012 | Kaib et al. | |
| 2012/0158075 A1 | 6/2012 | Kaib et al. | |
| 2012/0265265 A1 | 10/2012 | Razavi et al. | |
| 2012/0283794 A1 | 11/2012 | Kaib et al. | |
| 2012/0293323 A1 | 11/2012 | Kaib et al. | |
| 2012/0302860 A1 | 11/2012 | Volpe et al. | |
| 2012/0310315 A1 | 12/2012 | Savage et al. | |
| 2013/0085538 A1 | 4/2013 | Volpe et al. | |
| 2013/0231711 A1* | 9/2013 | Kaib | G16H 40/63 607/5 |
| 2013/0245388 A1 | 9/2013 | Rafferty et al. | |
| 2013/0274565 A1 | 10/2013 | Langer et al. | |
| 2013/0289637 A1* | 10/2013 | Amely-Velez | A61N 1/3956 607/60 |
| 2013/0317852 A1 | 11/2013 | Worrell et al. | |
| 2013/0325078 A1 | 12/2013 | Whiting et al. | |
| 2013/0325096 A1 | 12/2013 | Dupelle et al. | |
| 2014/0012144 A1 | 1/2014 | Crone | |
| 2014/0025131 A1 | 1/2014 | Sullivan et al. | |
| 2014/0046391 A1 | 2/2014 | Cowan et al. | |
| 2014/0070957 A1 | 3/2014 | Longinotti-Buitoni et al. | |
| 2014/0163663 A1 | 6/2014 | Poddar et al. | |
| 2014/0324112 A1 | 10/2014 | Macho et al. | |
| 2014/0378812 A1 | 12/2014 | Saroka et al. | |
| 2015/0039053 A1 | 2/2015 | Kaib et al. | |
| 2015/0328472 A1 | 11/2015 | Sullivan et al. | |
| 2016/0004831 A1 | 1/2016 | Carlson et al. | |
| 2016/0082277 A1 | 3/2016 | Foshee, Jr. et al. | |
| 2016/0256676 A1 | 9/2016 | Freeman | |
| 2019/0022400 A1 | 1/2019 | Kumar et al. | |
| 2019/0159696 A1 | 5/2019 | Meeker et al. | |
| 2022/0249854 A1 | 8/2022 | Ballard et al. | |
| 2022/0370788 A1 | 11/2022 | Freeman | |

OTHER PUBLICATIONS

LIFECOR LifeVest System Model WCD 3100 Operator's Manual, 2006, PN 20B0040 Rev FI, Zoll Lifecor Corporation, Pittsburgh, PA.

LifeVest Model 4000 Patient Manual, Zoll, 2009, PN 20B0047 Rev B.

Heartstart MRx and XL AED Algorithm—Application Note, Jul. 2001, Edition 2 Philips Healthcare, USA.

The LifeVest Network/Patient Data Management System, Zoll, 2015, 20C0503 Rev A.

Metting Van Rijn, A. C., Peper A., & Grimbergen, C. A., High-Quality Recording of Bioelectric Events Part 1: Interference Reduction, Theory and Practice, Review, Medical & Biological Engineering & Computing, Sep. 1990, pp. 389-397, IFMBE.

Pagan-Carlo, et al., "Encircling Overlapping Multipulse Shock Waveforms for Transthoracic Defibrillation," JACC Journals, Dec. 1998, vol. 32 Issue 7, p. 2065-2071.

(56) References Cited

OTHER PUBLICATIONS

ZOLL LifeVest Model 4000 Patient Manual PN 20B0047 Rev B, (C) 2009-2012.

* cited by examiner

WEARABLE CARDIOVERTER DEFIBRILLATOR LATCHING CONNECTOR

CROSS-REFERENCE TO RELATED APPLICATION

This application claims priority to and the benefit of U.S. Provisional Patent Application No. 62/630,995, filed Feb. 15, 2018 and is a continuation in part of U.S. application Ser. No. 16/277,838, filed Feb. 15, 2019, both of which are incorporated herein by reference in their entirety for all purposes.

SUMMARY

The present disclosure generally relates to wearable cardioverter defibrillator ("WCD") systems. WCD systems have become a standard of care for patients who may be candidates for a future implantable defibrillator but do not currently meet the criteria for such a device. WCDs act as a bridge between an event such as a myocardial infarction or ex-plantation of an implantable cardioverter defibrillator ("ICD") and when the patient is a viable candidate for a new implant. WCD systems may monitor the patient's electrocardiography ("ECG") signals twenty-four hours a day, continuously processing them to determine if defibrillation therapy is needed. WCD systems often include monitors that contain elements of the WCD system (e.g., electronics) and facilitate a patient's (or other user's) understanding of how the WCD system is operating. WCD systems may include connector systems that electrically and physically connect different components. For example, a connector system may electrically and physically connect a WCD monitor to an electrode for attachment to a patient.

In an embodiment, the present disclosure provides a WCD latching connector system for incorporation into a WCD system, the WCD latching connector system providing a shielded connection and incorporating water seals to resist water ingress. The WCD latching system has a receptacle positioned within a WCD monitor and extending through an outer wall of the WCD monitor, and a connector configured to removably engage the receptacle.

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

DESCRIPTION OF THE DRAWINGS

The foregoing aspects and many of the attendant advantages of this disclosure will become more readily appreciated as the same become better understood by reference to the following detailed description, when taken in conjunction with the accompanying drawings and appendix, wherein.

DETAILED DESCRIPTION

The detailed description set forth below in connection with the appended drawings is intended as a description of various embodiments of the disclosed subject matter and is not intended to represent the only embodiments. Each embodiment described in this disclosure is provided merely as an example or illustration and should not be construed as preferred or advantageous over other embodiments. The illustrative examples provided herein are not intended to be exhaustive or to limit the claimed subject matter to the precise forms disclosed.

Figure 1:
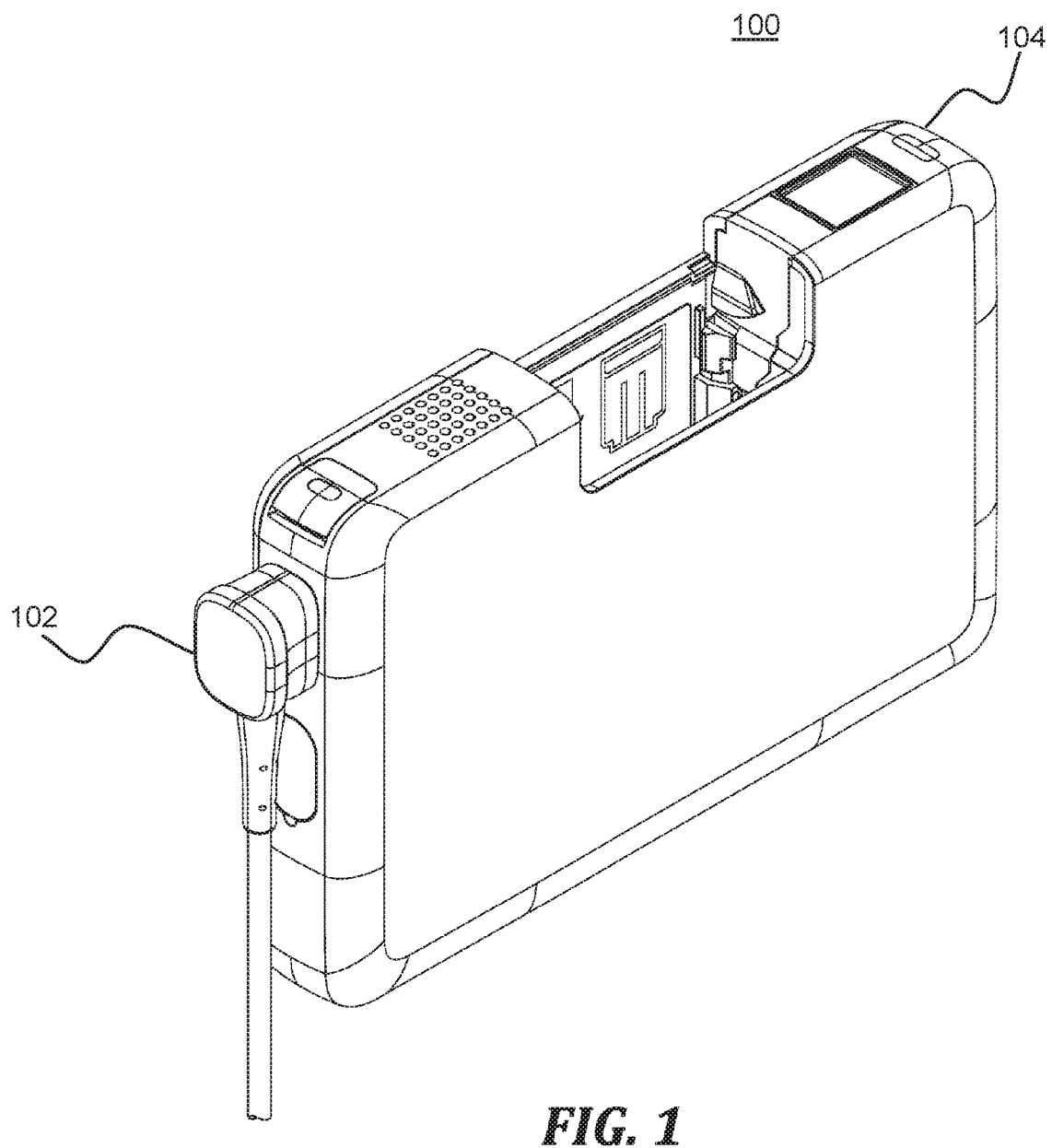
FIG. 1 is a perspective view of a Wearable Cardioverter Defibrillator ("WCD") latching connector system of the present disclosure.
Figure 2:
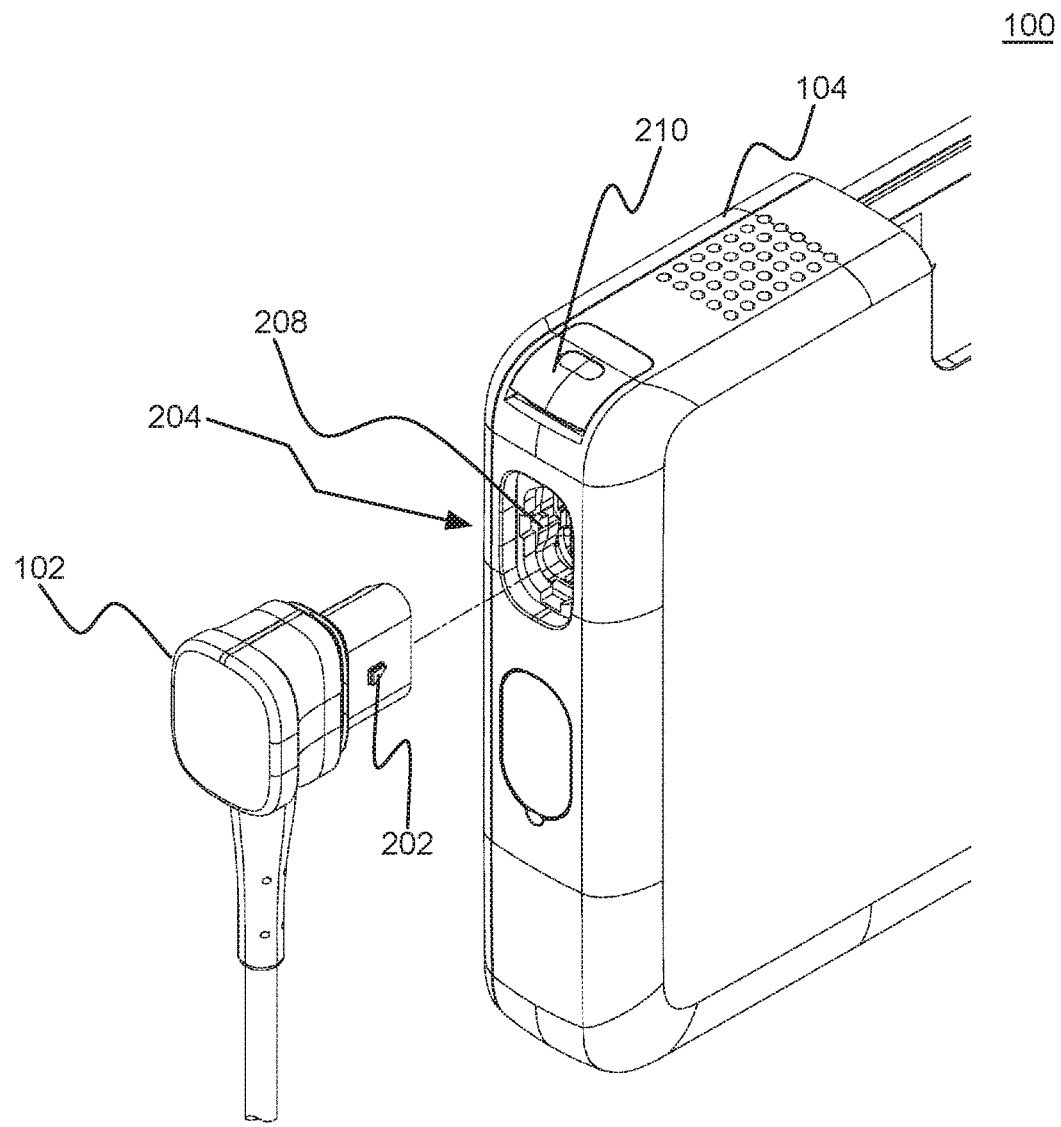
FIG. 2 is an exploded partial perspective view of the WCD latching connector system of FIG. 1.

Referring to FIGS. 1-2, a wearable cardioverter defibrillator ("WCD") system includes a WCD latching connector system that is partially integrated with a WCD monitor. The WCD system may include additional elements, including a plurality of electrodes configured for connection to a patient and to the WCD monitor, and a harness or vest for positioning the electrodes on the body of the patient.

Figure 3:
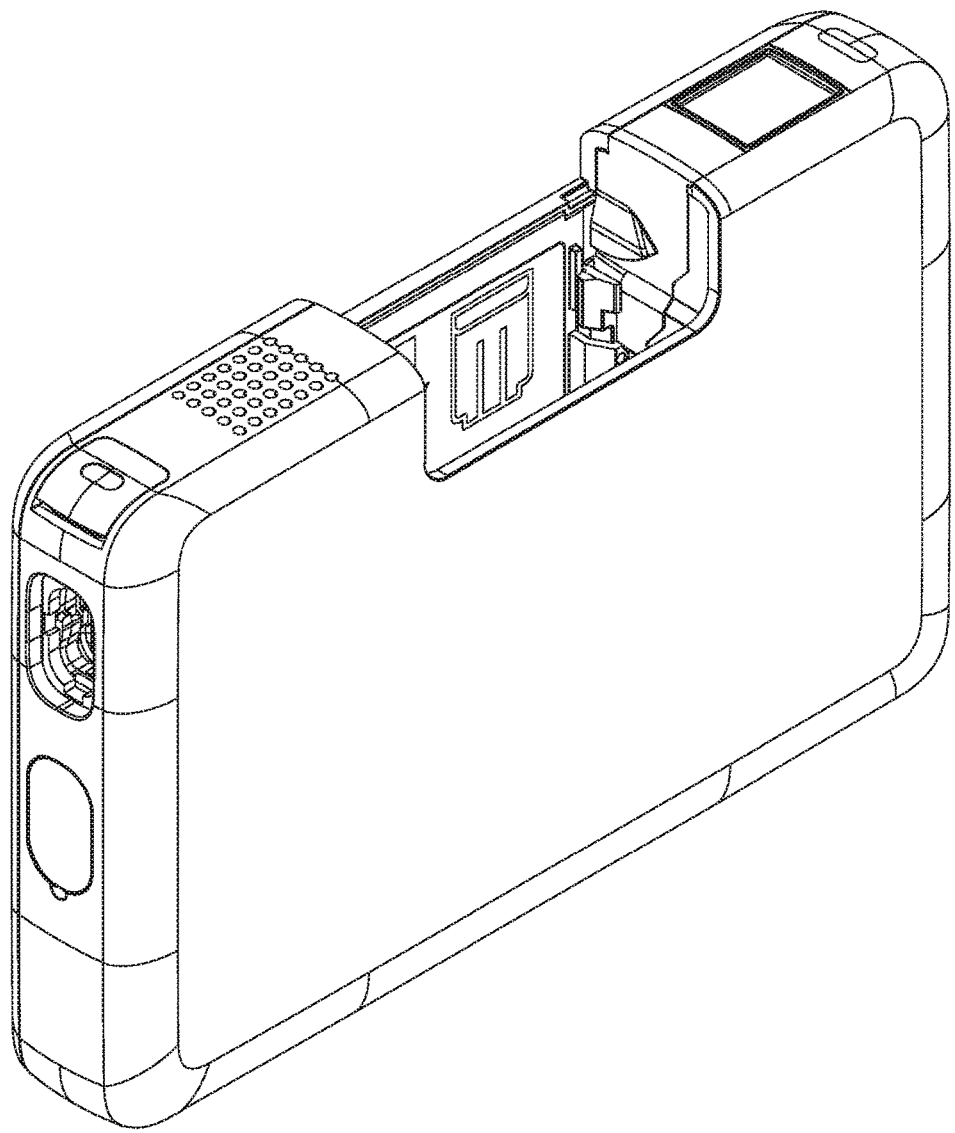
FIG. 3 is a perspective view of an aspect of the WCD latching connector system of FIG. 1.
Figure 4:
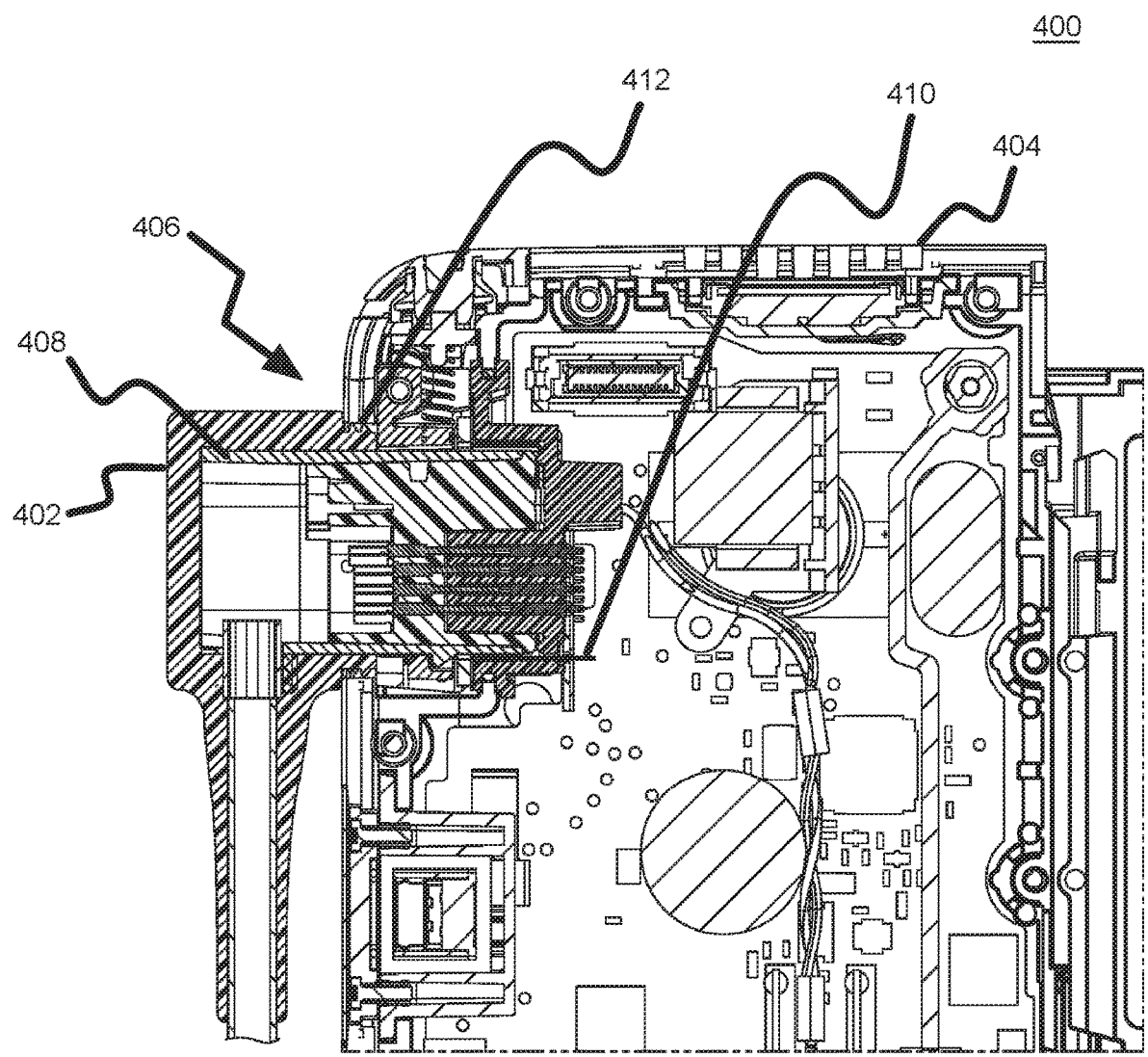
FIG. 4 is a partial section view of the WCD latching connector system of FIG. 1.
Figure 5:
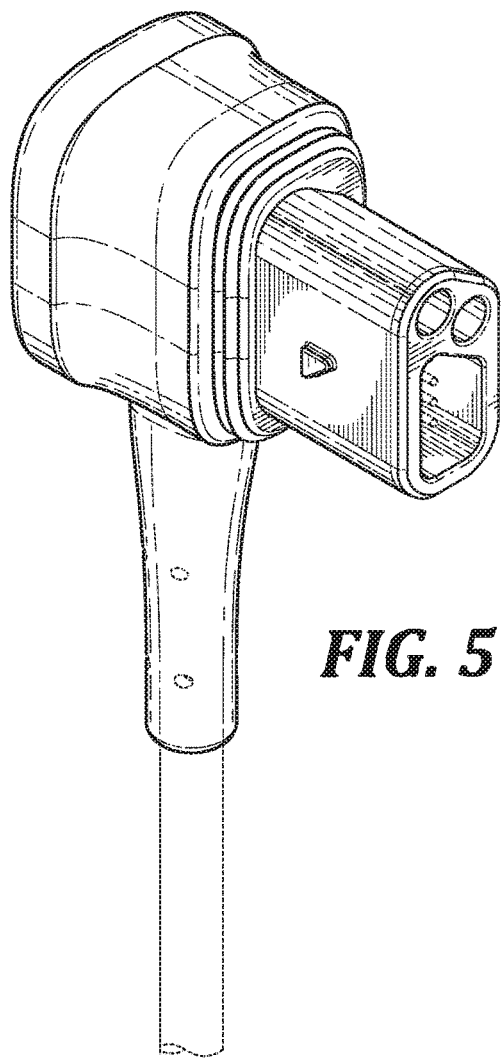
FIG. 5 is a first perspective view of a WCD connector of the WCD latching connector system of FIG. 1.
Figure 6:
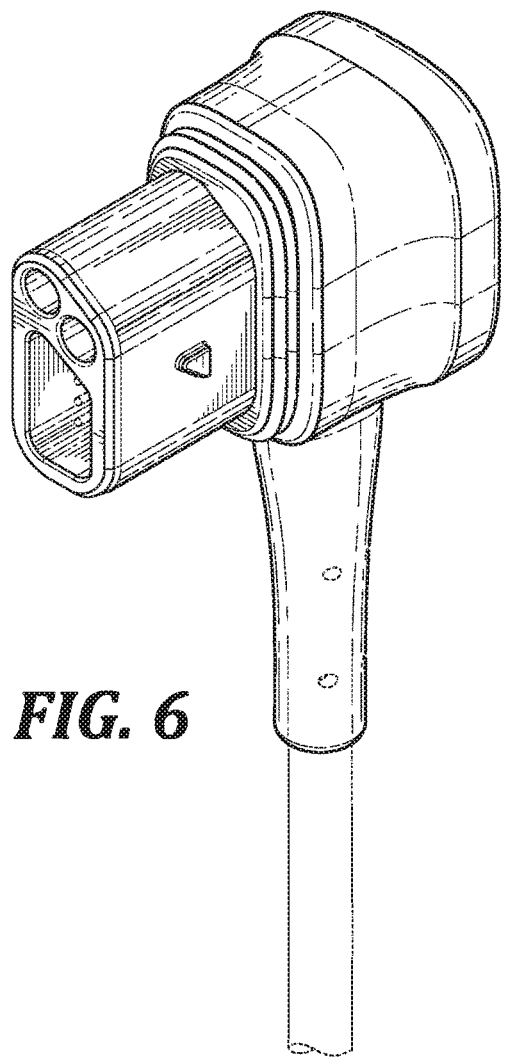
FIG. 6 is a second perspective view of the WCD connector of FIG. 5.
Figure 7:
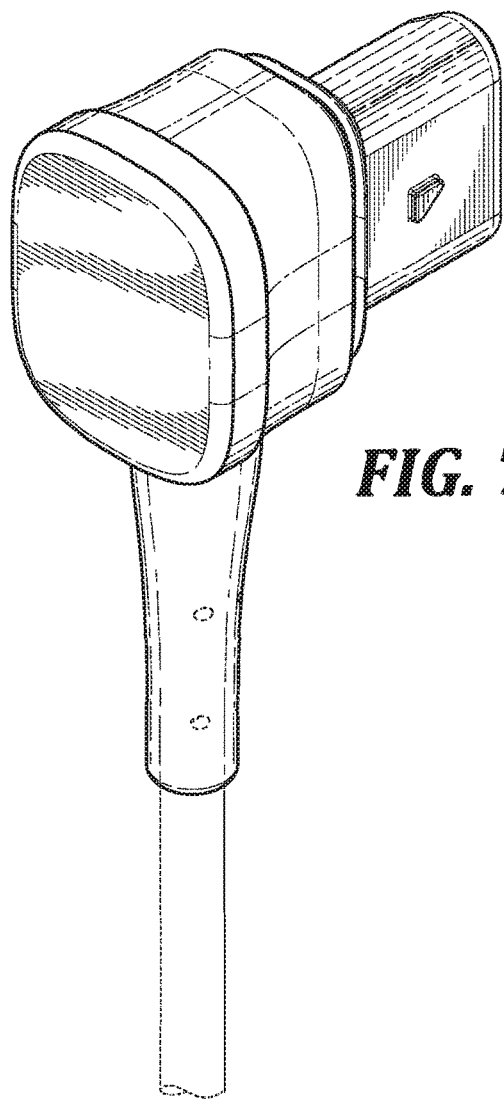
FIG. 7 is a third perspective view of the WCD connector of FIG. 5.
Figure 8:
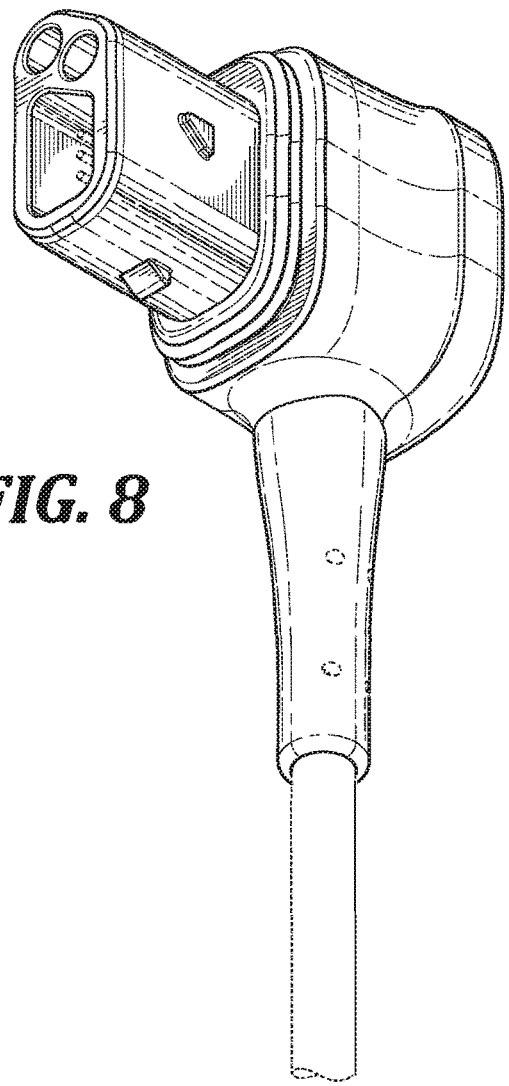
FIG. 8 is a fourth perspective view of the WCD connector of FIG. 5.

The WCD monitor shown in FIG. 3 includes an enclosure assembly that is configured to protect defibrillator electronics contained therein (electronics are partially shown in FIG. 4). The enclosure assembly may be a multi-piece assembly that includes a housing, a front cover, and a rear cover. The housing generally lies in between the front cover and the rear cover. The housing, the front cover, and the rear cover may each be constructed from one or more durable materials capable of withstanding shocks, abrasions, and other forces likely to be encountered when the WCD monitor is worn by a patient. In the non-limiting embodiment of FIGS. 1-4, the enclosure assembly is primarily constructed of one or more plastics, for example acrylonitrile butadiene styrene and/or polycarbonate.

Referring again to FIG. 2, the WCD latching connector system includes a connector and a receptacle configured to form a shielded physical and electrical connection therebetween. The connector has one or more latches, a shield (such as a metal shield), and a connector overmold. The receptacle extends through an outer wall of the WCD monitor, and includes a chamber having one or more electrical connections. The receptacle houses a shield (such as a metal shield) and a latch configured to engage the one or more latches on the connector.

In use, the WCD latching connector system may electrically and physically connect, for example, patient-facing electrodes and the WCD monitor. Other applications are contemplated. The WCD latching connector system incorporates water seals to resist ingress of water. The connector may be removably inserted into the receptacle, where it engages the WCD monitor as shown in the partial section view of FIG. 4. When the connector is inserted into the receptacle, a latch of the receptacle engages a latch of the connector, locking the connector to the receptacle. To remove the connector, a button on the WCD monitor is depressed, thereby unlatching the connector from the receptacle and enabling removal of the connector from the connector.

In an embodiment, the button includes a membrane (e.g., an elastomeric membrane) to prevent water from entering the receptacle, and in particular a chamber within the receptacle. In an embodiment, the WCD latching connector system includes one or more high voltage (HV) connections for defibrillation therapy along with one or more low voltage connections. In an embodiment, the WCD latching connector system includes a mating shield connection in the connector and receptacle that ensures the LV and HV signals remain intact in electrically noisy environments. In an embodiment, the WCD latching connector system includes a latching system as described above that locks the connector to the receptacle and requires a button to be depressed in order to unlatch the connector to remove the connector. An embodiment may have any single or combination of the above features. In an embodiment, the WCD latching connector system includes a connector overmold to create a water seal on the WCD housing system when inserted into the receptacle to further resist liquid from entering the receptacle chamber.

FIGS. 5-15 generally show an exemplary connector of the WCD latching connector system of FIGS. 1-4. FIGS. 16-26 generally show another exemplary connector of a WCD latching connector system of the present disclosure.

Advantages of the disclosed WCD latches connector system include actively locking the connector into the receptacle of the WCD monitor, electrically shielding the LV and HV connections to improve signal quality and sealing the receptacle chamber from water ingress.

Having described and disclosed the various embodiments above with respect to the claimed subject matter, some further details may be described below.

Referring back to FIGS. 1 and 2, some shown features may be described in further detail. For example, as shown in FIG. 1, the WCD system 100 may include a WCD connector 102 coupled with a WCD monitor 104. Turning now to FIG. 2, the WCD connector 102 may be shown separated from the WCD monitor 104 exposing one or more tabs 202 on the WCD connector 102. The WCD connector 102 may couple with the WCD monitor 104 via a receptacle 204 incorporated into the WCD monitor 104. The WCD connector 102 may be coupled to the WCD monitor 104 by inserting the WCD connector 102 into the receptacle 204, where one or more tabs 202 on the WCD connector 102 may facilitate securely coupling the WCD connector 102 with the WCD monitor 104.

In FIG. 2, the receptacle 204 may include latching features 208. Additionally, shown on a corner proximate to the receptacle 204 may be a button 210. The latching features 208 may be configured to facilitate latching of the WCD connector 102 with the WCD monitor 104. For example, in FIG. 2, the one or more tabs 202 may be configured to engage the latching feature 208 such as, but not limited to, a slide and catch mechanism. That is, the WCD connector 104 may be pushed into the receptacle 204, where the one or more tabs 202 may mechanically engage with the latching features 208 with the latching features 208 engages the one or more tabs 202 helping to prevent removal of the WCD connector 102 from the receptacle 204 forming a water resistance seal and an electrically shielded connection. As shown, the WCD connector 102 may be released from the WCD monitor 104 by depressing the button 210, which may actuate the latching features 208 to release the one or more tabs 202 facilitating removal of the WCD connector 102 from the receptacle 204. Accordingly, the one or more tabs 202 may be part of the latching system with a complimentary latching receiver (latching features 208) included in the WCD monitor 104 to facilitate a relatively sealed coupling of various electrical coupling components.

Referring back to FIG. 4, some shown features may be described in further detail. In FIG. 4, the WCD latching connector system 400 includes a WCD connector 402 and a WCD monitor 404. As shown, the WCD connector 402 may be coupled with the WCD monitor 404 by inserting the WCD connector 402 into a receptacle 406. Additionally, shown in FIG. 4, the WCD connector 402 may have a shield, a connector shield 408 with the WCD monitor 404 having a shield of its own, a monitor shield 410. The connector shield 408 and the monitor shield 410 may be configured to facilitate shielding of the connection between the WCD connector 402 and the WCD monitor 404.

The connector shield 408 may be made of metals such as, but not limited to, magnesium-zinc alloy, aluminum alloy, or zinc alloy. In one example, the connector shield 408 may be made of a die cast zinc alloy part with nickel plating to help facilitate corrosion resistance. One the WCD monitor 404, the monitor shield 410 may also be made of metals such as, but not limited to, magnesium-zinc alloy, aluminum alloy, zinc alloy, beryllium-based alloys. In one example, the monitor shield 410 may be made of beryllium copper alloy, which may also facilitate corrosion resistance. Additionally, the beryllium copper alloy may facilitate reduction of fatigue of the monitor shield 410 due to deflection during engagement with the connector shield 408 (e.g., the monitor shield 410 may deflect and spring back for many cycles of engagement with the connector shield 408). The connector shield 408 and the monitor shield 410 may facilitate shielding of various electrical coupling components, thereby facilitating shielding of the electrical signals from noise and various artifacts, in accordance with various embodiments.

Another feature shown in FIG. 4 may be some baffle like structures 412 to facilitate prevention of ingress of water as described. As may be appreciated, the ingress of water or water prevention may be expressed as Ingress Protection (e.g., IP or IPX rating). In accordance with the present disclosure, the IP rating may be between IPX2 and IPX4. That is, the WCD connector 402 and the WCD monitor 404 may have an IP rating of IPX2 to IPX4, respectively.

As previously described, the non-limiting embodiment of FIGS. 1-4, the enclosure assembly is primarily constructed of one or more plastics, for example acrylonitrile butadiene styrene and/or polycarbonate. For example, briefly turning back to FIG. 2, the latching features 208 inside the receptacle 204 of the WCD monitor 104 may be made of a combination of plastic type material such as, but not limited to, a Polyoxymethylene based engineered thermoplastic (e.g., Derlin® available from Dupont de Nemours, Inc.), Polybutylene Terephthalate (PBT) (e.g., glass filled PBT), Polycarbonate/Acrylonitrile Butadiene Styrene (PC/ABS), and/or any combination thereof. The choice of the above example plastic type materials may be based, at least in part, on consideration for how the plastic type materials may interact with one another. For example, the referring to the latching connector system (e.g., one or more tabs 202 and latching features 208), some of the moving parts of the latching feature 208 may be made of PBT, while the other parts may be made of Derlin®. This combination may help to reduce the potential for chemical bonding (e.g., between the plastic parts) or covalent bonding. Embodiments of the WCD latching connector system may include combinations and sub-combinations of features described or shown in the drawings herein, including for example, embodiments that are equivalent to: providing or applying a feature in a different order than in a described embodiment, extracting an individual feature from one embodiment and inserting such feature into another embodiment; removing one or more features from an embodiment; or both removing one or more features from an embodiment and adding one or more features extracted from one or more other embodiments, while providing the advantages of the features incorporated in such combinations and sub-combinations. As used in this paragraph, feature or features can refer to the structures and/or functions of an apparatus, article of manufacture or monitor, and/or the steps, acts, or modalities of a method.

Figure 9:
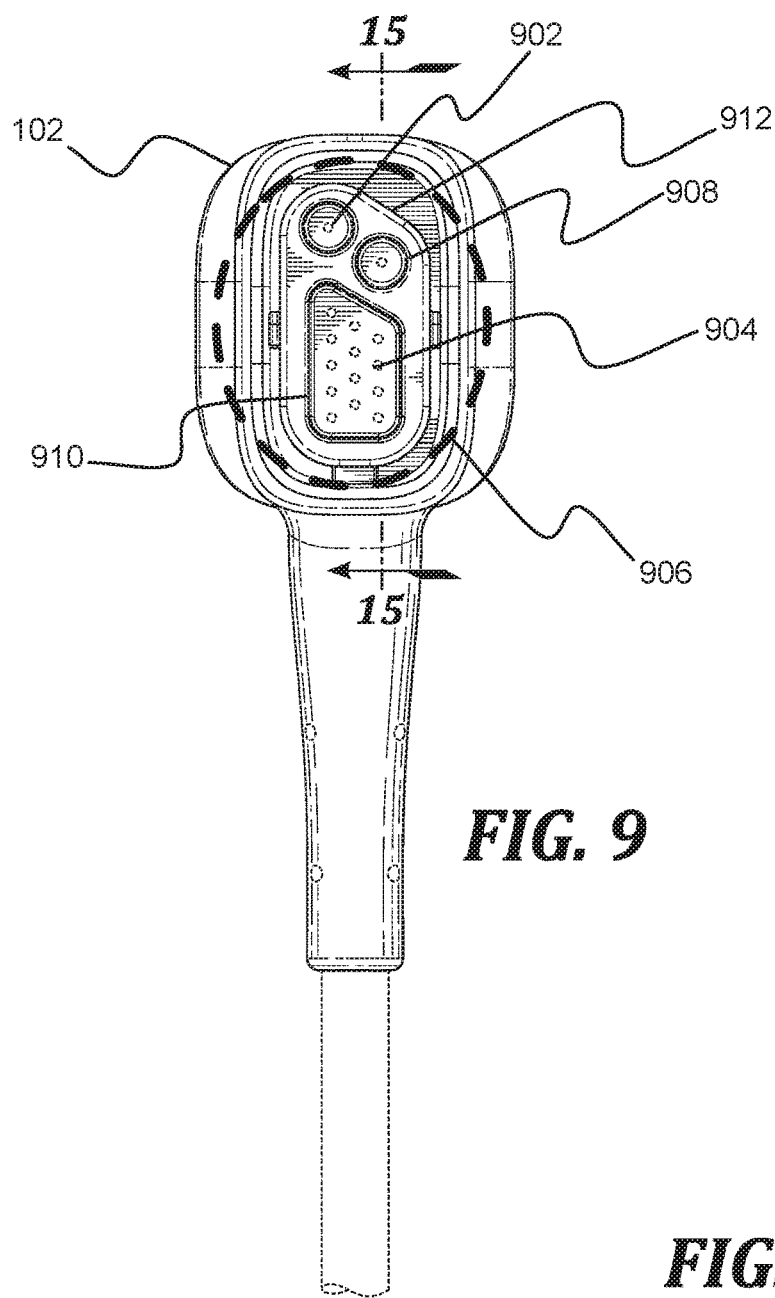
FIG. 9 is a front view of the WCD connector of FIG. 5.
Figure 10:
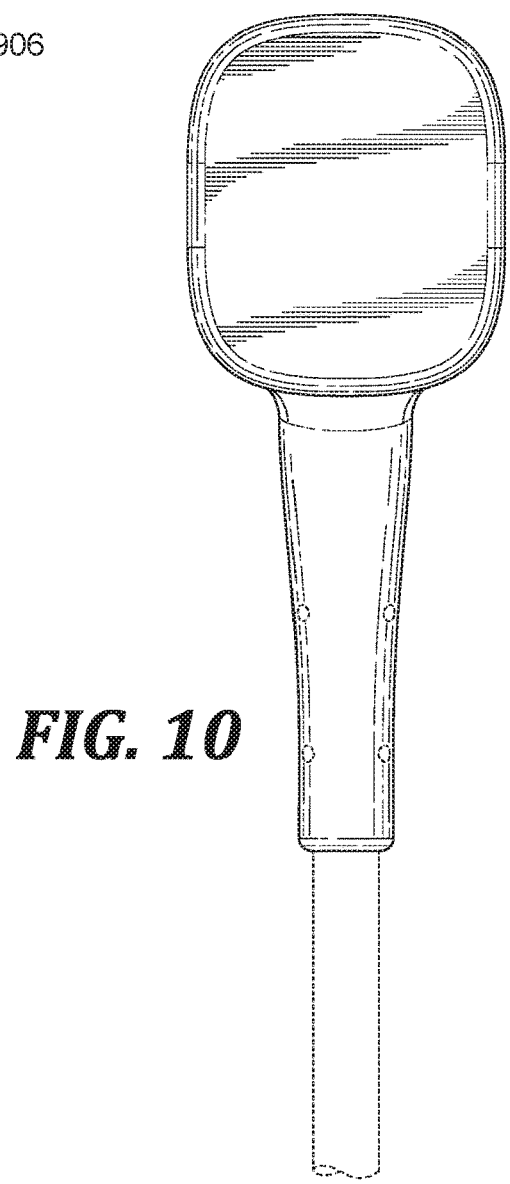
FIG. 10 is a rear view of the WCD connector of FIG. 5.
Figure 11:
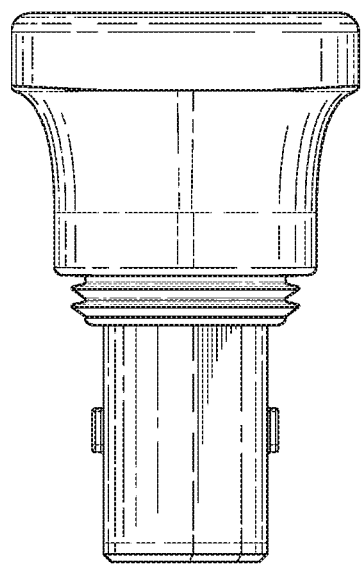
FIG. 11 is a top view of the WCD connector of FIG. 5.
Figure 12:
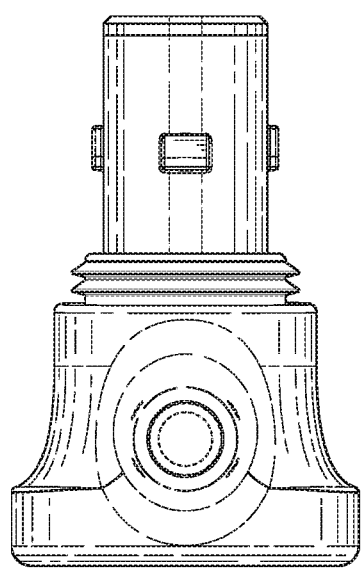
FIG. 12 is a bottom view of the WCD connector of FIG. 5.
Figure 13:
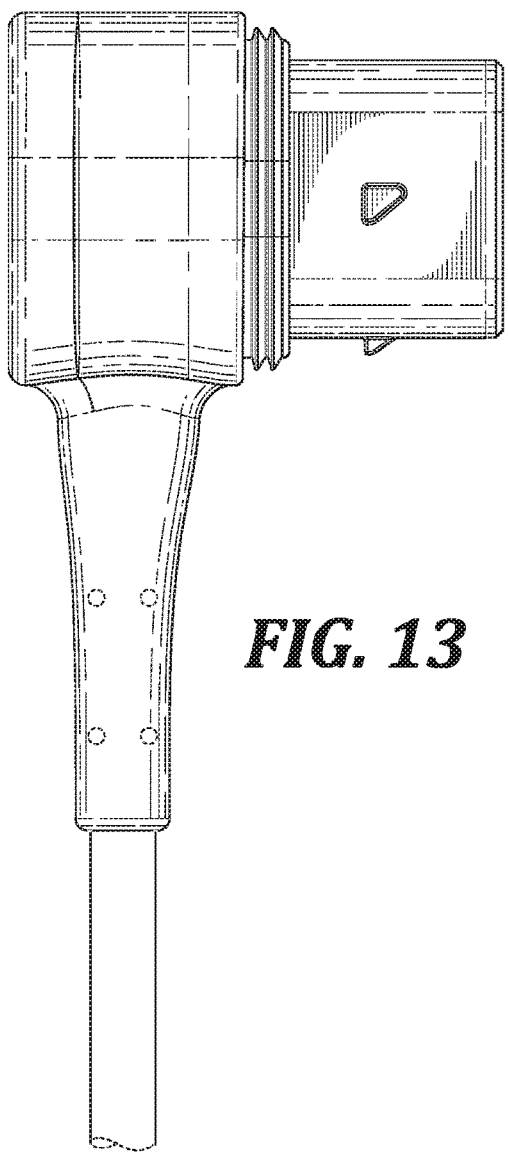
FIG. 13 is a right view of the WCD connector of FIG. 5.
Figure 14:
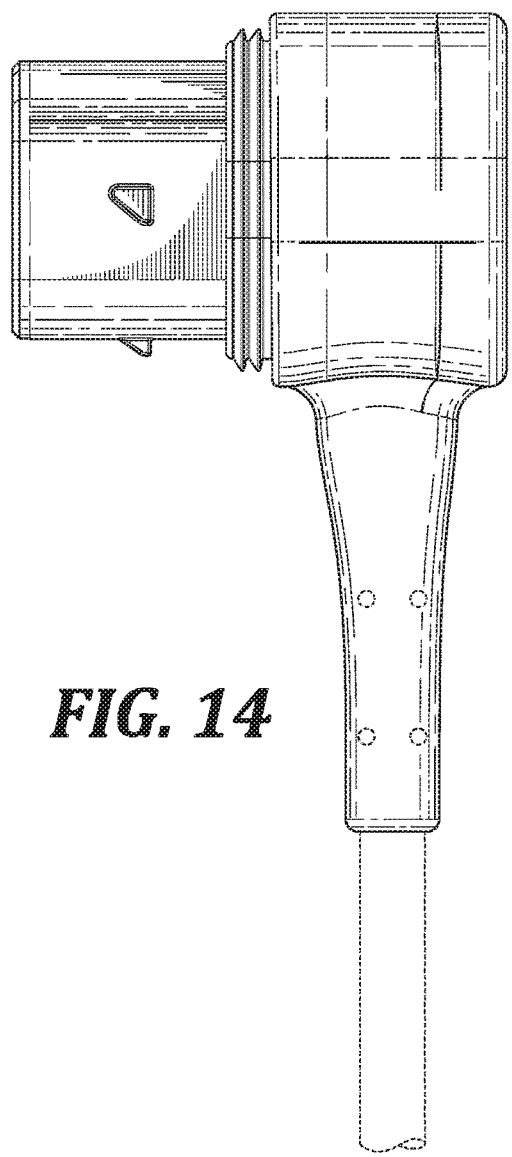
FIG. 14 is a left view of the WCD connector of FIG. 5.
Figure 15:
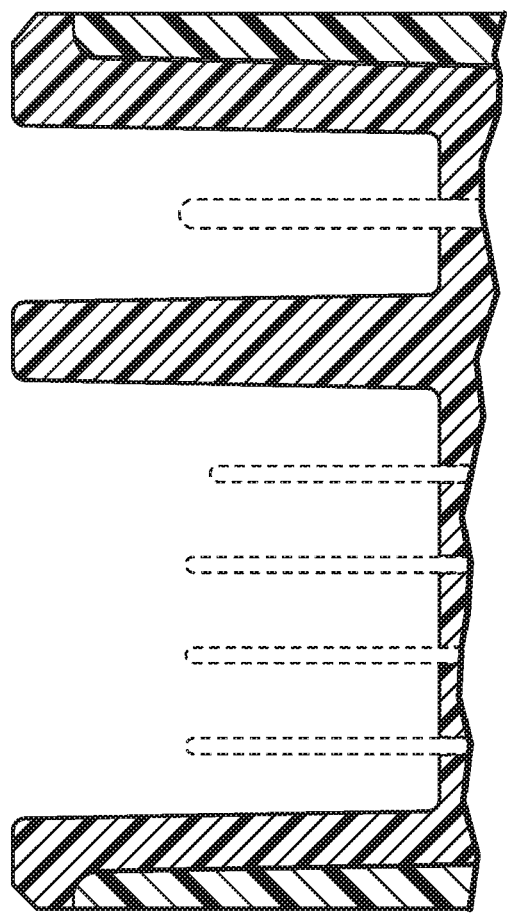
FIG. 15 is a partial section view of the WCD connector of FIG. 5.
Figure 16:
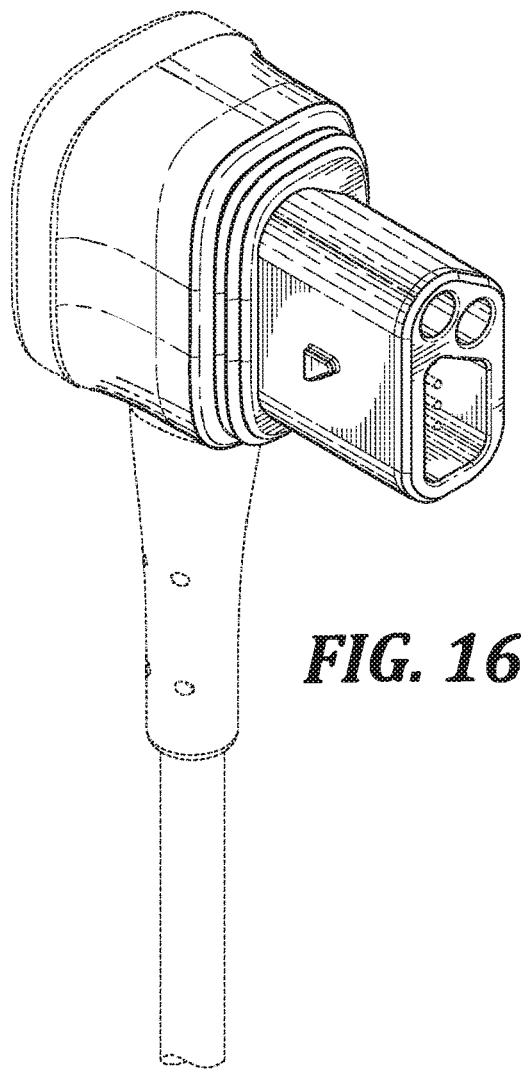
FIG. 16 is a first perspective view of another WCD connector of a WCD latching connector system of the present disclosure.
Figure 17:
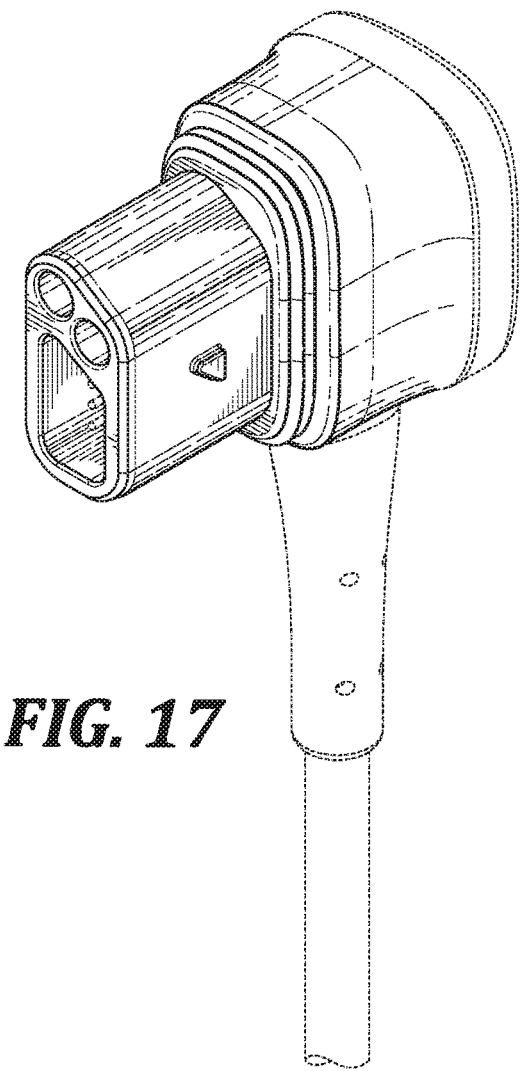
FIG. 17 is a second perspective view of the WCD connector of FIG. 16.
Figure 18:
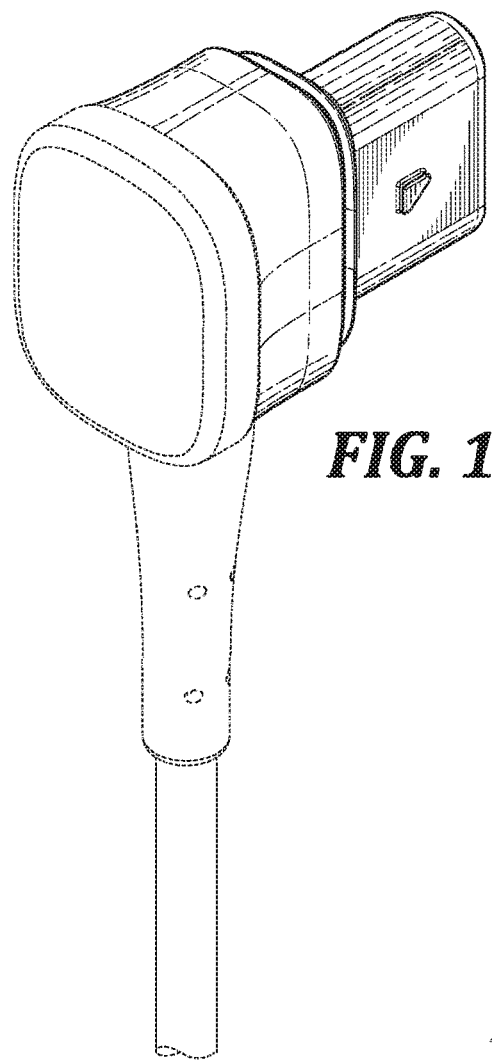
FIG. 18 is a third perspective view of the WCD connector of FIG. 16.
Figure 19:
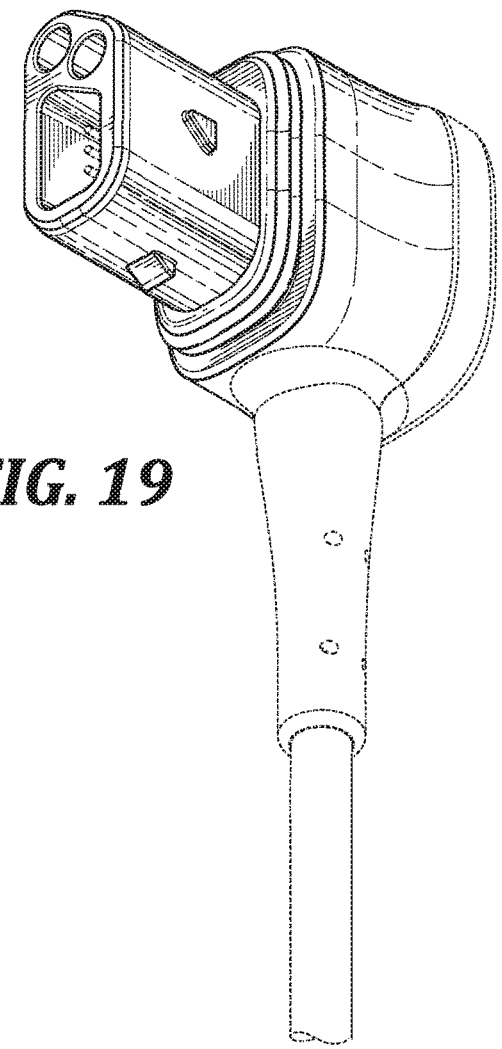
FIG. 19 is a fourth perspective view of the WCD connector of FIG. 16.
Figure 20:
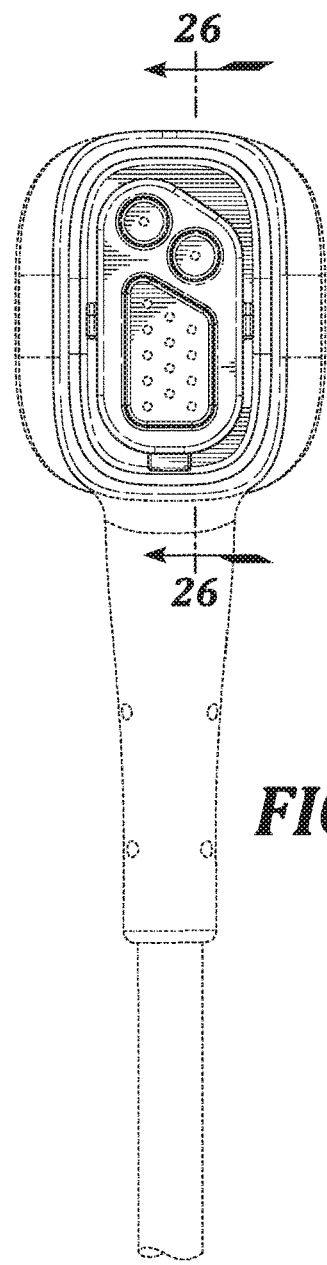
FIG. 20 is a front view of the WCD connector of FIG. 16.
Figure 21:
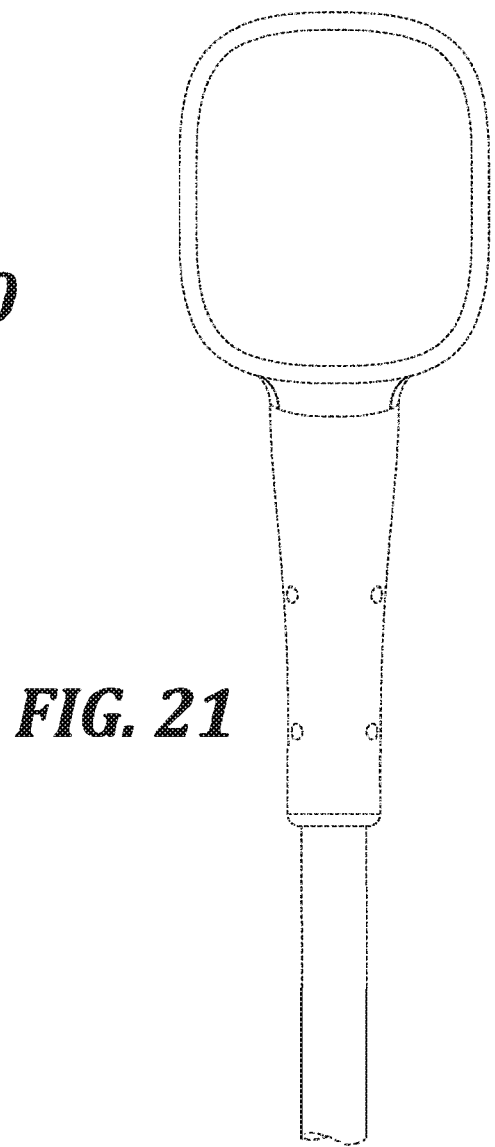
FIG. 21 is a rear view of the WCD connector of FIG. 16.
Figure 22:
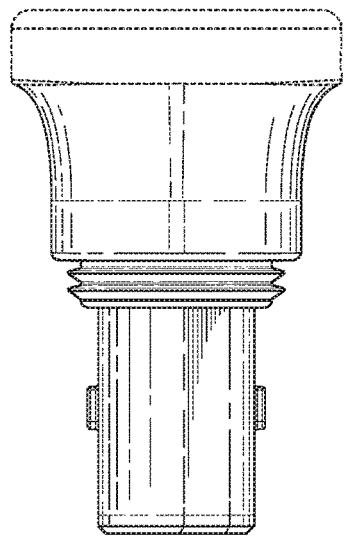
FIG. 22 is a top view of the WCD connector of FIG. 16.
Figure 23:
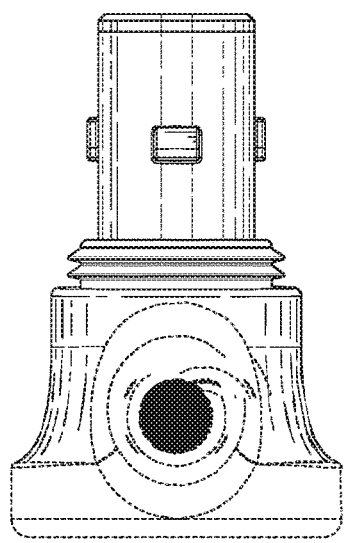
FIG. 23 is a bottom view of the WCD connector of FIG. 16.
Figure 24:
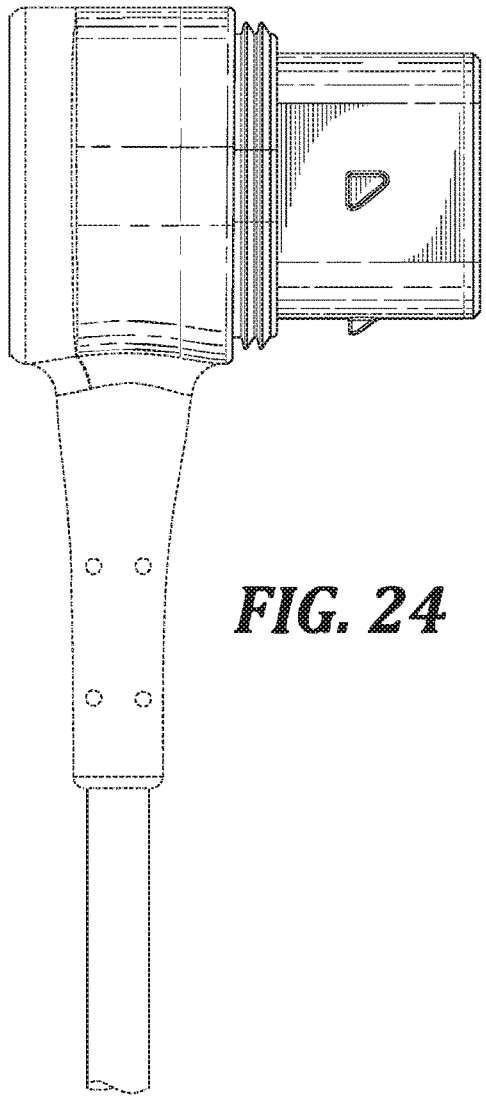
FIG. 24 is a right view of the WCD connector of FIG. 16.
Figure 25:
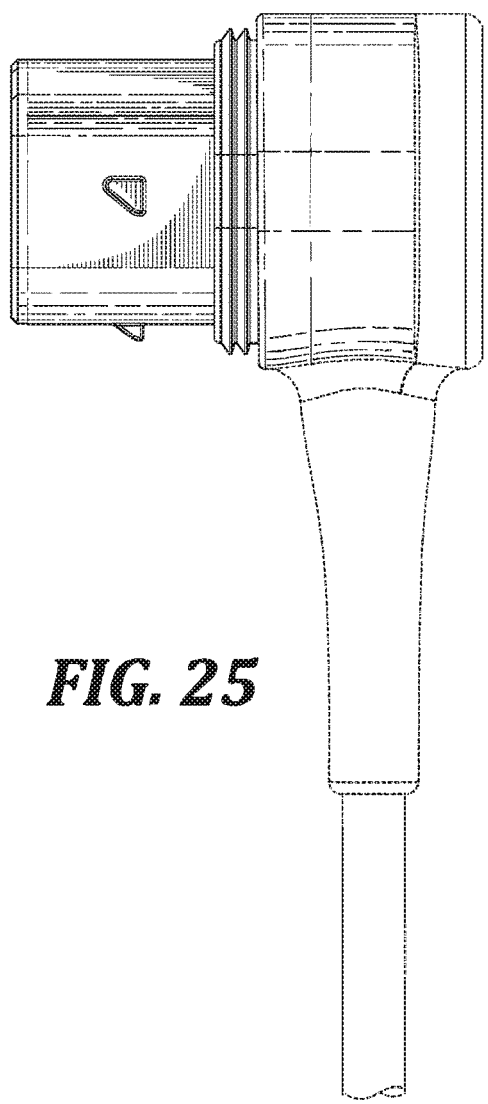
FIG. 25 is a left view of the WCD connector of FIG. 16.
Figure 26:
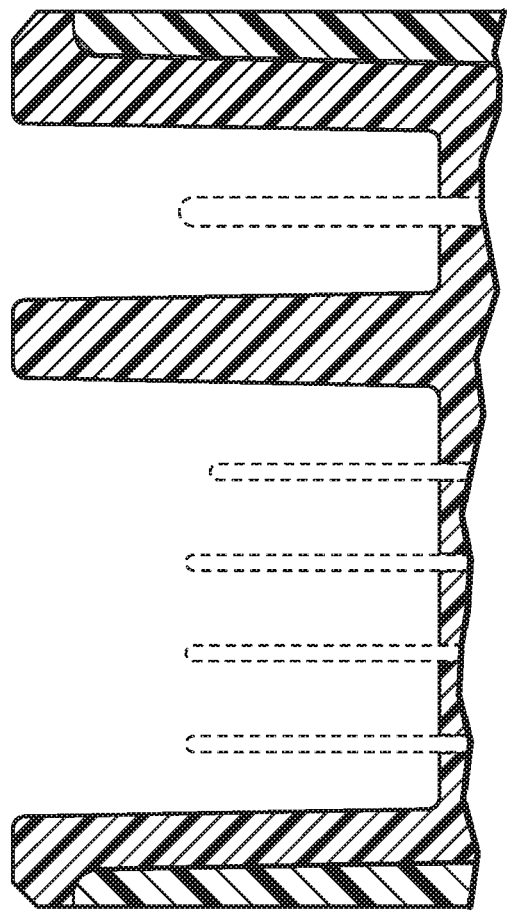
FIG. 26 is a partial section view of an aspect of the WCD connector of FIG. 16.
Figure 28:
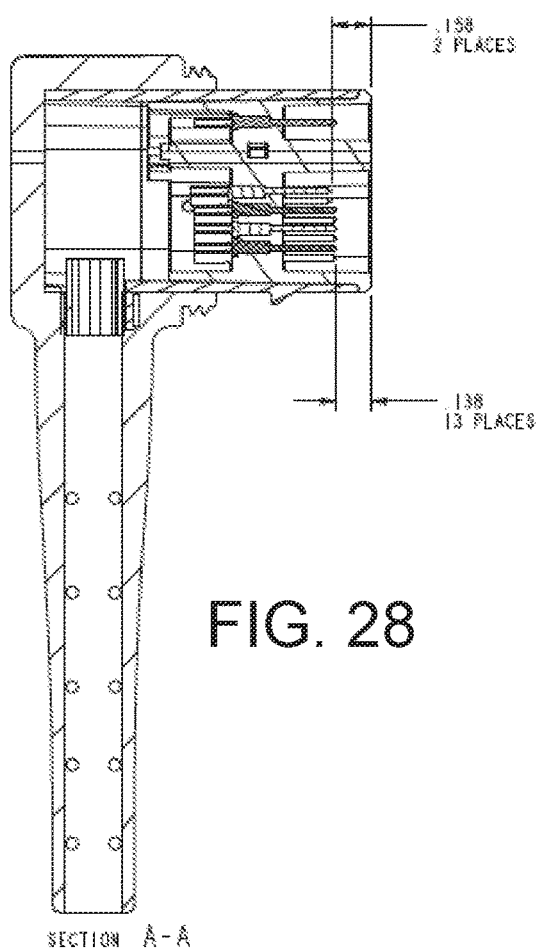
FIG. 28 is a cross sectional view of the WCD connector of FIG. 27.
Figure 27:
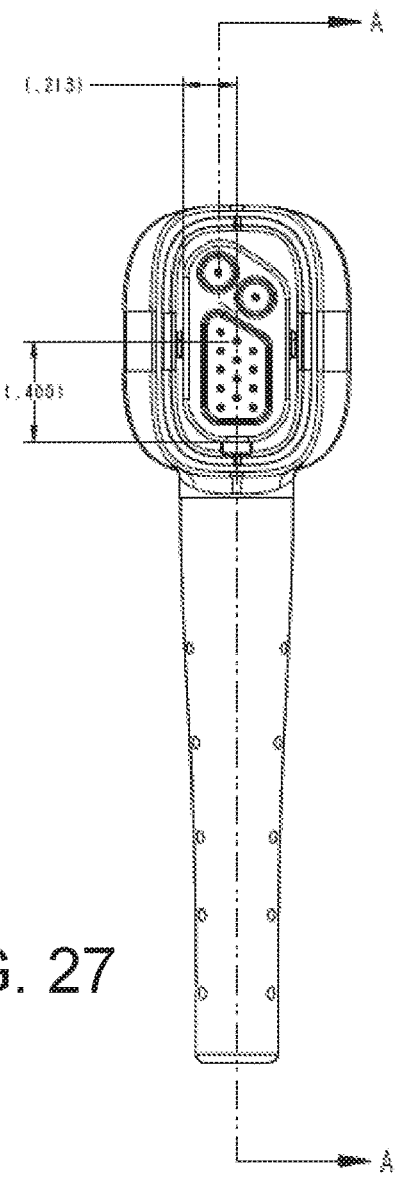
FIG. 27 is a front view of a WCD connector of FIG. 9.
Figure 29:
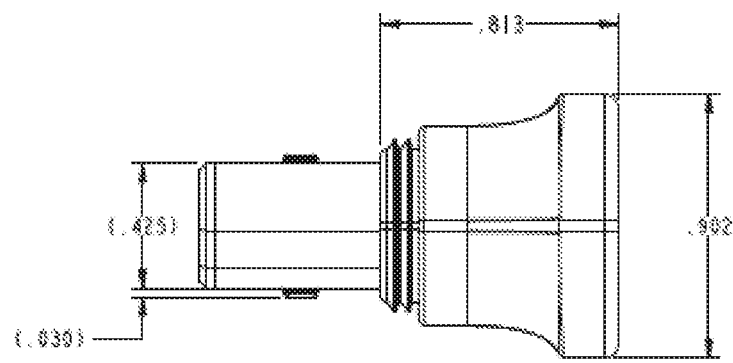
FIG. 29 is a top view of the WCD connector of FIG. 27.
Figure 30:
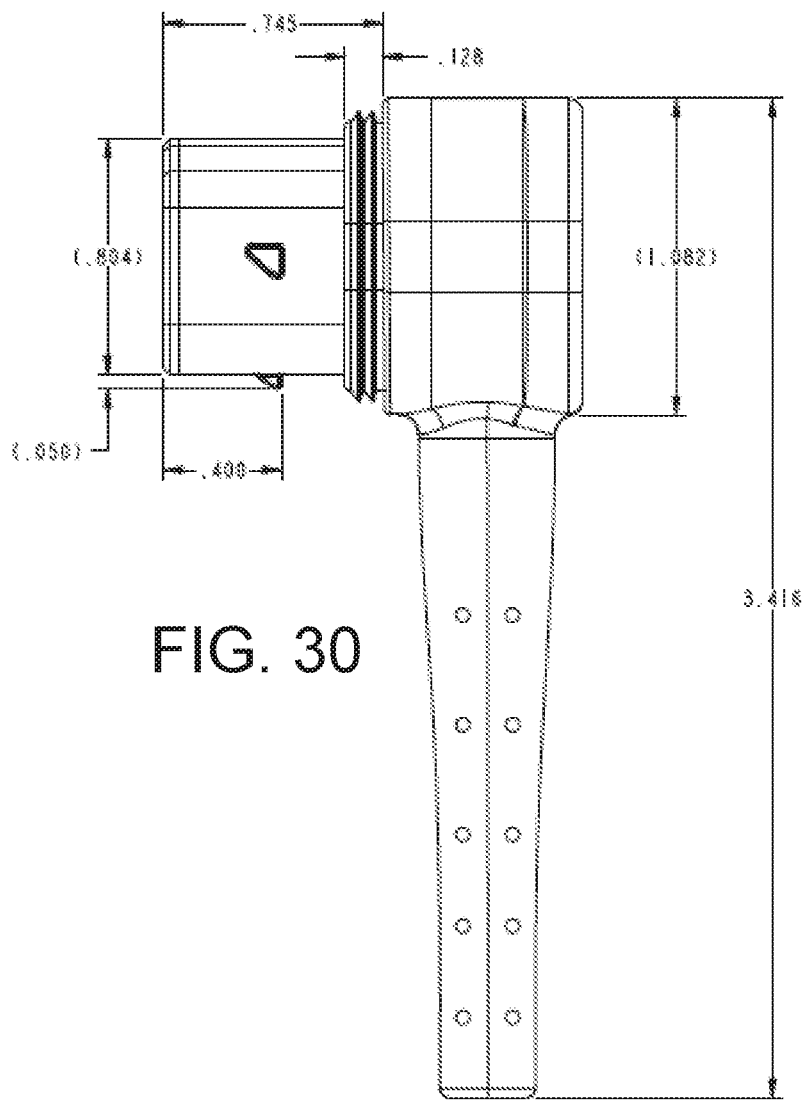
FIG. 30 is a left view of the WCD connector of FIG. 27.

Referring back to FIG. 9, in the head on view of the WCD connector 102, electrical connection pins may be clearly shown. The electrical connection pins may include two high voltage connection pins 902 and 13 low voltage connection pins 904. As shown, each of the two high voltage connection pins 902 may be separated by a first plastic feature 908. The 13 low voltage connection pins 904 may be collectively separated by a second plastic feature 910. The first and second plastic features 908 and 910 may be configured to facilitate control of creepage and clearance distances between each of the two high voltage connection pins 902 and between the two high voltage connections pins 902 with the 13 low voltage connection pins 904. In FIG. 9, the overall layout of the two high voltage connection pins 902 and the 13 low voltage connection pins 904 may be in a shape that may be described as a trapezoidal type shape 906 (e.g., approximately a right trapezoidal shape). The 13 low voltage connection pins 904 (i.e., the second plastic feature 910) may have a layout that substantially follows the trapezoidal type shape 906 with the two high voltage connection pins 902 being aligned along a sloping side 912 of the trapezoidal type shape 906. In accordance with various embodiments, the layout of the two high voltage connection pins 902 and the 13 low voltage connection pins 904 including the first plastic feature 908 and the second plastic feature 910 in the trapezoidal type shape 906 helps facilitate control of creepage and clearance distances along with a relatively small form factor. As previously described, the connector shielding 408 (shown in FIG. 4) may be configured to substantially surround the electrical connection pins 902 and 904. It should be appreciated that number of pins for the both the high voltage connections pins 902 low voltage connection pins 904 may vary based at least, in part, on the application (e.g., type of wearable medical device). That is, the number of electrical connection pins may vary (e.g., two high electrical connection pins and 7 or more electrical connection pins), and accordingly, the claimed subject matter is not limited in this respect.

FIGS. 27-30 illustrates various views of a WCD connector, in accordance with a non-limiting example. In the non-limiting examples shown in FIGS. 27-30, the WCD connector may have example dimension to facilitate distances between the various components. For example, the non-limiting dimensions shown in FIGS. 27-30 may help facilitate management of arching and electrostatic discharge in dielectric materials. Accordingly, the example dimensions shown in FIGS. 27-30 may facilitate clearance and creepage distances of the electrical connection pins (e.g., the high voltage connection pins 902), as described above with respect to FIG. 9. Additionally, in order to facilitate management of arching and electrostatic discharge in dielectric materials, the materials for the various components of the WCD connector 102 may include dielectric materials such as, but not limited to, low density polyethylene, polyimide, etc. It should be appreciated that example dimensions shown in FIGS. 27-30 may vary based, at least in part, on the number of electrical connection pins electrical connection pins 902 and 904 (shown in FIG. 9), and accordingly, the example dimensions shown in FIGS. 27-30 are but an example and is not limiting to the scope of the disclosed subject matter.

Figure 31:
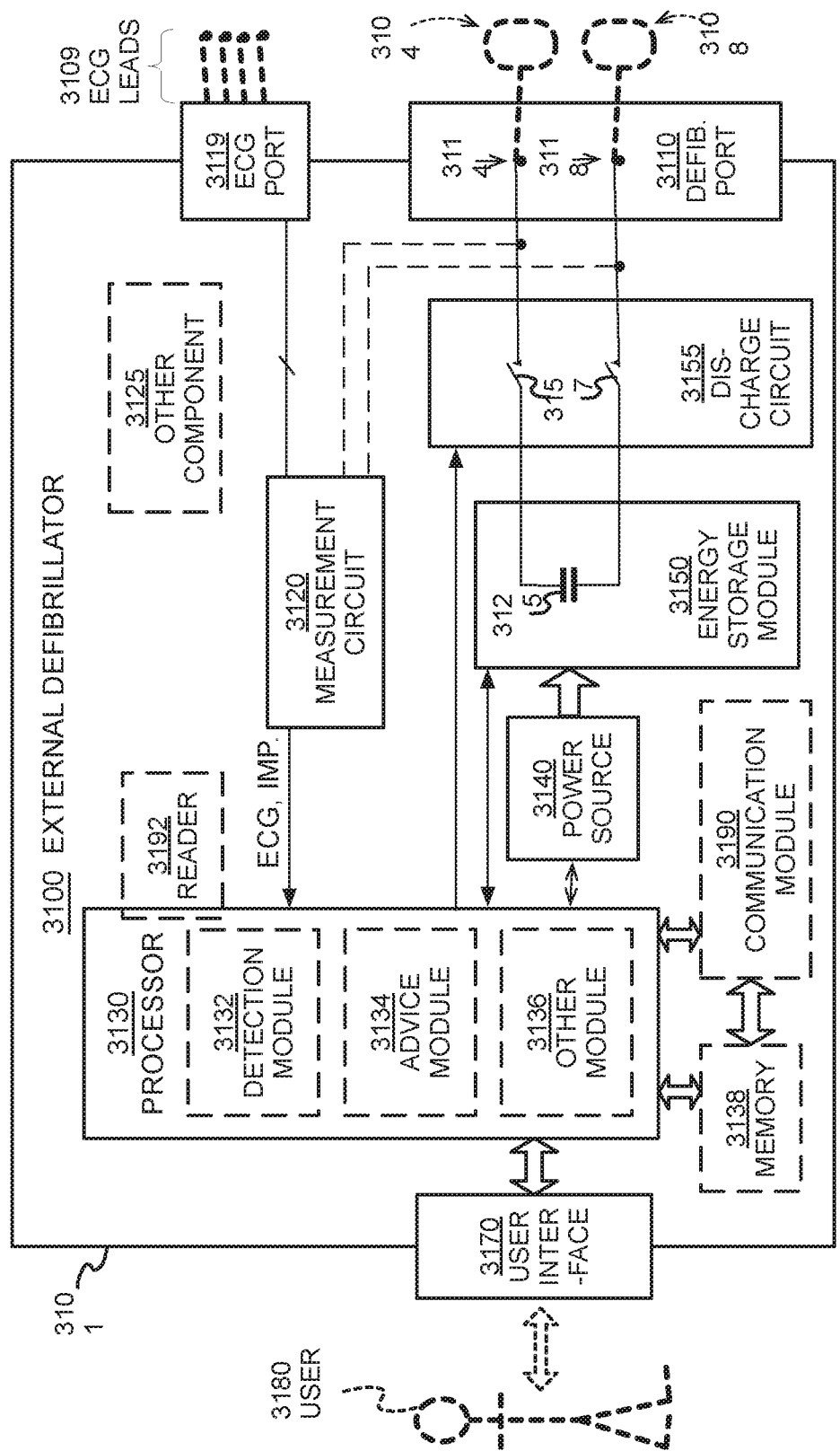
FIG. 31 is a block diagram illustrating components of a defibrillator device, which may be used with various embodiments.

FIG. 31 is a block diagram illustrating components of a defibrillator device, which may be used with various embodiments. These components may be, for example, components of a WCD system 100 and 400 (shown in FIGS. 1 and 4).

The defibrillator device 3100 may be some of the above examples of one or more WCD systems 100 and 400 intended for use by a user 3180. The defibrillator device 3100 may typically include a defibrillation port 3110, such as a socket in housing 3101 (e.g., latching connector system in FIGS. 1-4). The defibrillation port 3110 may include nodes 3114 and 3118. One or more electrodes 3104 and 3108, which may be plugged into the defibrillation port 3110, so as to make electrical contact with nodes 3114 and 3118, respectively. It may also be possible that the electrodes 3104 and 3108 may be connected continuously to the defibrillation port 3110, etc. Either way, the defibrillation port 3110 may be used for guiding via the electrodes 3104 and 3108 to a person 3180 an electrical charge that may have been stored in the defibrillator device 3100, as described herein.

The defibrillator device 3100 may also have an ECG port 3119 in the housing 3101 (e.g., WCD monitor 104 and 400 in FIGS. 1-4), for receiving ECG cables 3109. The ECG cables 3109 may facilitate sensing of an ECG signal (e.g., a 12-lead signal or from a different number of lead signals). Moreover, a defibrillator-monitor could have additional ports (not shown), and the other component 3125 may be configured to filter the ECG signal (e.g., application of at least one filter to the signal to help facilitate removal of artifacts such as, but not limited to, chest compression due to chest compressions being delivered to the person).

The defibrillator 3100 also may include a measurement circuit 3120. The measurement circuit 3120 may receive physiological signals from the ECG port 3119, and also from other ports, if provided. The circuit 3120 may render detected physiological signals and their corresponding information. The information may be in the form of data, or other signals, etc.

If the defibrillator 3100 is configured as a WCD type device (shown in FIGS. 1-4), ECG port 3119 may not be present. The measurement circuit 3120 may obtain physiological signals through the nodes 3114 and 3118 instead, when the electrodes 3104 and 3108 are attached to the person 3180. In these cases, a person's ECG signal may be detected as a voltage difference between the electrodes 3104 and 3108. Additionally, the impedance between the electrodes 3104 and 3108 may be detected, among other things, whether the electrodes 3104 and 3108 have been inadvertently disconnected from the person 3180.

The defibrillator 3100 may also include a processor 3130. The processor 3130 may be implemented in a wide variety of manners for causing actions and operations to be performed. Some examples may include digital and/or analog processors such as microprocessors and digital-signal processors (DSPs), controllers such as microcontrollers, software running in a machine environment, programmable circuits such as Field Programmable Gate Arrays (FPGAs), Field-Programmable Analog Arrays (FPAAs), Programmable Logic Devices (PLDs), Application Specific Integrated Circuits (ASICs), and so on or any combination thereof.

The processor 3130 may include a number of modules. One example module may be a detection module 532, which may detect outputs from the measurement circuit 3120. The detection module 3132 may include a VF detector. Accordingly, the person's detected ECG may be utilized to help determine whether the person is experiencing ventricular fibrillation (VF).

In another example module may be an advice module 3134, which may provide advice based, at least in part, on outputs of detection module 532. The advice module 3134 may include an algorithm such as, but not limited to, Shock Advisory Algorithm, implement decision rules, and so on. For example, the advice may be to shock, to not shock, to administer other forms of therapy, and so on. If the advice is to shock, some defibrillator examples may report the advice to the user, and prompt them to do it. In other examples, the defibrillator device may execute the advice by administering the shock. If the advice is to administer CPR, the defibrillator 3100 may further issue prompts for administrating CPR, and so forth.

The processor 3130 may include additional modules, such as module 3136 for various other functions. Additionally, if other component 3125 is provided, it may be operated in part by processor 3130, etc.

In an example, the defibrillator device 3100 may include a memory 3138, which may work together with the processor 3130. The memory 3138 may be implemented in a wide variety of manners. For example, the memory 3138 may be implemented such as, but not limited to, nonvolatile memories (NVM), read-only memories (ROM), random access memories (RAM), and so forth or any combination thereof. The memory 3138 may can include programs for the processor 3130, and so on. The programs may include operational programs execution by the processor 530 and may also include protocols and methodologies that decisions may be made by advice module 3134. Additionally, the memory 3138 may store various prompts for the user 3180, etc. Moreover, the memory 3138 may store a wide variety of information (i.e., data) such as, but not limited to information regarding the person.

The defibrillator 3100 may also include a power source 3140. In order to facilitate portability of defibrillator device 3100, the power source 3140 may include a battery type device. A battery type device may be implemented as a battery pack, which may be rechargeable or not be rechargeable. At times, a combination of rechargeable and non-rechargeable battery packs may be utilized. Examples of power source 3140 may include AC power override, where AC power may be available, and so on. In some examples, the processor 3130 may control the power source 3140.

Additionally, the defibrillator device 3100 may include an energy storage module 3150. The energy storage module 3150 may be configured to store some electrical energy (e.g., when preparing for sudden discharge to administer a shock). The energy storage module 3150 may be charged from the power source 3140 to an appropriate level of energy, as may be controlled by the processor 3130. In some implementations, the energy storage module 3150 may include one or more capacitors 3152, and the like.

The defibrillator 3100 may include a discharge circuit 3155. The discharge circuit 3155 may be controlled to facilitate discharging of the energy stored in energy storage module 3150 to the nodes 3114 and 3118, and also to electrodes 3104 and 3108. The discharge circuit 3155 may include one or more switches 3157. The one or more switches 3157 may be configured in a number of manners such as, but not limited to, an H-bridge, and so forth.

The defibrillator device 3100 may further include a user interface 3170 for the user 3180. The user interface 3170 may be implemented in a variety of manners. For example, the user interface 3170 may include a display screen capable of displaying what is detected and measured, provide visual feedback to the user 3180 for their resuscitation attempts, and so forth. The user interface 3170 may also include an audio output such as, but not limited to, a speaker to issue audio prompts, etc. The user interface 3170 may additionally include various control devices such as, but not limited to, pushbuttons, touch display, and so forth. Additionally, the discharge circuit 3155 may be controlled by the processor 3130 or directly by the user 3180 via the user interface 3170, and so forth.

Additionally, the defibrillator device 3100 may include other components. For example, a communication module 3190 may be provided for communicating with other machines and/or the electrodes. Such communication may be performed wirelessly, or via wire, or by infrared communication, and so forth. Accordingly, information may be communicated, such as person data, incident information, therapy attempted, CPR performance, ECG information, and so forth.

It should be appreciated after review of this disclosure that it is contemplated within the scope and spirit of the present disclosure that the claimed subject matter may include a wide variety of clips, materials, mechanical shapes, etc. Accordingly, the claimed subject matter is not limited in these respects.

In some portions of the description, illustrative implementations of the disclosure may have been described with reference to the elements of the components described with respect to FIGS. 1-31. However, the described embodiments are not limited to these depictions. More specifically, some elements/components depicted in FIGS. 1-31 may be omitted from some implementations detailed herein. Furthermore, other elements not depicted in FIGS. 1-31 may be used to implement example apparatuses detailed herein.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

While illustrative embodiments have been illustrated and described, it will be appreciated that various changes can be made therein without departing from the spirit and scope of this disclosure. The present application may reference directions, e.g., top, bottom, front, back, left, and right. These references are intended only to aid in understanding of the embodiments, and do not limit the orientation, location, position, of any feature of the embodiments, or otherwise limit the scope of the present disclosure.

The present application may also reference quantities and numbers. Unless specifically stated, such quantities and numbers are not to be considered restrictive, but exemplary of the possible quantities or numbers associated with the present application. Also, in this regard, the present application may use the term "plurality" to reference a quantity or number. In this regard, the term "plurality" is meant to be any number that is more than one, for example, two, three, four, five, etc. The terms "about," "approximately," "near," etc., mean plus or minus 5% of the stated value. For the purposes of the present disclosure, the phrase "at least one of A, B, and C," for example, means (A), (B), (C), (A and B), (A and C), (B and C), or (A, B, and C), including all further possible permutations when greater than three elements are listed.

The principles, representative embodiments, and modes of operation of the present disclosure have been described in the foregoing description. However, aspects of the present disclosure which are intended to be protected are not to be construed as limited to the particular embodiments disclosed. Further, the embodiments described herein are to be regarded as illustrative rather than restrictive. It will be appreciated that variations and changes may be made by others, and equivalents employed, without departing from the spirit of the present disclosure. Accordingly, it is expressly intended that all such variations, changes, and equivalents fall within the spirit and scope of the present disclosure, as claimed.

What is claimed is:

1. A wearable cardioverter defibrillator (WCD) system comprising:
   a WCD monitor having a receptacle, the WCD monitor configured to deliver high voltage (HV) signals and receive low voltage (LV) signals, wherein the HV signals comprise a defibrillating electrical shock for delivery to a person and the LV signals comprise electrocardiogram (ECG) signals from the person;
   a first mating shield disposed within the receptacle;
   a latching feature disposed within the receptacle;
   a WCD connector that comprises one or more structures configured to prevent ingress of water into the receptacle, wherein the WCD connector is configured to latchably couple with the latching feature, the WCD connector having a second mating shield configured to mate with the first mating shield, the mated first and second mating shields configured to substantially shield the HV signals and the LV signals from electrical noise.

2. The WCD system of claim 1, wherein the one or more structures are configured to prevent the ingress of water to an Ingress Protection (IP) rating of IPX2 to IPX4.

3. The WCD system of claim 1, wherein the second mating shield comprises a metal shield disposed around a plurality of electrical pins of the WCD connector.

4. The WCD system of claim 3, wherein the metal shield comprises a die cast zinc alloy with nickel plating.

5. The WCD system of claim 1, wherein the first mating shield comprises a metal shield having one or more resilient mating structures to electrically contact the first mating shield.

6. The WCD system of claim 5, wherein the metal shield comprises a beryllium copper alloy.

7. The WCD system of claim 1, wherein the latching feature comprises movable parts configured to latch with the WCD connector.

8. The WCD system of claim 7, wherein the movable parts comprise of one or more movable parts made of engineered thermoplastic selected to reduce chemical bonding of the movable parts.

9. The WCD system of claim 1, wherein the WCD connector comprises one or more tabs configured to latch with the latching feature of the WCD monitor.

10. The WCD system of claim 1, wherein the WCD connector comprises a plurality of HV pins and LV pins.

11. The WCD system of claim 10, wherein the plurality of HV pins and the LV pins are arranged in a substantially trapezoidal layout.

12. The WCD system of claim 1, wherein the one or more structures comprise baffle like structures.

13. A wearable cardioverter defibrillator (WCD) connector comprising:
   a plurality of low voltage (LV) electrical pins, the plurality of LV electrical pins configured to receive LV signals from a person, the LV signals include electrocardiogram (ECG) signals from the person;
   a plurality of voltage (HV) electrical pins, the configured to deliver HV signals to the person, the HV signals comprising a defibrillating shock to the person;
   one or more electrical shields disposed around the plurality of LV and HV electrical pins; and
   one or more tabs disposed on sides of the WCD connector configured to latchably couple the WCD connector in a receptacle of a WCD monitor.

14. The WCD connector of claim 13, wherein the plurality of LV electrical pins and HV electrical pins are arranged in a substantially trapezoidal layout.

15. The WCD connector of claim 13 further comprising one or more structures configured to prevent ingress of water into the receptacle of the WCD monitor.

16. The WCD connector of claim 13, wherein the one or more electrical shields comprises a metal shield configured to mate with an electrical shield of the receptacle of the WCD monitor.

17. A wearable cardioverter defibrillator (WCD) monitor comprising:
   a housing;
   a receptacle included in the housing, the receptacle configured to receive a WCD connector that comprises one or more structures configured to prevent ingress of water into the receptacle;

a plurality of low voltage (LV) receptacle contacts, the plurality of LV receptacle contacts configured to receive a plurality of LV electrical pins and receive via the plurality of LV electrical pins LV signals having electrocardiogram (ECG) signals from a person;

a plurality of high voltage (HV) receptacle contacts, the plurality of HV receptacle contacts configured to receive a plurality of HV electrical pins and deliver via the plurality of HV electrical pins HV signals to the person, the HV signals comprising a defibrillating shock;

a latching feature disposed within the receptacle, the latching feature configured to latchably couple with the WCD connector; and a shield, the shield included within the receptacle and configured to electrically shield the LV signals and the HV signals electrical signals from electrical noise between the WCD monitor and the WCD connector.

18. The WCD monitor of claim 17, wherein the shield comprises a metal shield having one or more resilient mating structures configured to electrically contact an electrical shield of the WCD connector when the WCD connector is received in the receptacle.

19. The WCD monitor of claim 18, wherein the metal shield comprises a beryllium copper alloy.

20. The WCD monitor of claim 17 further comprising a button configured to latch and unlatch the WCD connector from the receptacle.

* * * * *